(12) United States Patent
Babayoff et al.

(10) Patent No.: US 8,638,447 B2
(45) Date of Patent: Jan. 28, 2014

(54) METHOD AND APPARATUS FOR IMAGING THREE-DIMENSIONAL STRUCTURE

(75) Inventors: Noam Babayoff, Rishon Le Zion (IL); Isaia Glaser-Inbari, Givataim (IL)

(73) Assignee: Cadent Ltd., Or Yehuda (IL)

( * ) Notice: Subject to any disclaimer, the term of this patent is extended or adjusted under 35 U.S.C. 154(b) by 0 days.

(21) Appl. No.: 13/619,906

(22) Filed: Sep. 14, 2012

(65) Prior Publication Data

US 2013/0094031 A1    Apr. 18, 2013

Related U.S. Application Data

(60) Continuation of application No. 13/082,623, filed on Apr. 8, 2011, now Pat. No. 8,310,683, which is a continuation of application No. 12/654,699, filed on Dec. 29, 2009, now Pat. No. 7,944,569, which is a continuation of application No. 12/314,064, filed on Dec. 3, 2008, now Pat. No. 7,796,277, which is a continuation of application No. 11/652,055, filed on Jan. 11, 2007, now Pat. No. 7,477,402, which is a continuation of application No. 11/377,403, filed on Mar. 17, 2006, now Pat. No. 7,230,725, which is a continuation of application No. 11/175,186, filed on Jul. 7, 2005, now Pat. No. 7,092,107, which is a continuation of application No. 10/692,678, filed on Oct. 27, 2003, now Pat. No. 6,940,611, which is a division of application No. 09/775,298, filed on Feb. 1, 2001, now Pat. No. 6,697,164, which is a continuation of application No. PCT/IL99/00431, filed on Aug. 5, 1999.

(30) Foreign Application Priority Data

Aug. 5, 1998 (IL) ......................................... 125659

(51) Int. Cl.
*G01B 11/24* (2006.01)

(52) U.S. Cl.
USPC ........................................................... 356/609

(58) Field of Classification Search
USPC .......................................... 356/601, 603, 609
See application file for complete search history.

(56) References Cited

U.S. PATENT DOCUMENTS

| | | | |
|---|---|---|---|
| 3,013,467 A | | 12/1961 | Minsky |
| 3,812,505 A | * | 5/1974 | Elliott ............................. 396/21 |
| 4,257,688 A | | 3/1981 | Matsumura |
| 4,443,706 A | | 4/1984 | DiMatteo et al. |

(Continued)

FOREIGN PATENT DOCUMENTS

| | | |
|---|---|---|
| DE | 4035799 A1 | 5/1992 |
| DE | 19537586 A1 | 4/1997 |

(Continued)

OTHER PUBLICATIONS

Bertin, "Sensors," 1996, p. 17.

(Continued)

*Primary Examiner* — Roy M Punnoose
(74) *Attorney, Agent, or Firm* — Wilson Sonsini Goodrich & Rosati

(57) ABSTRACT

An apparatus for determining surface topology of a portion of a three-dimensional structure is provided, that includes a probing member, an illumination unit, a light focusing optics, a translation mechanism, a detector and a processor.

25 Claims, 5 Drawing Sheets

(56) References Cited

U.S. PATENT DOCUMENTS

| | | | |
|---|---|---|---|
| 4,575,805 A | 3/1986 | Moermann et al. | |
| 4,585,349 A | 4/1986 | Gross et al. | |
| 4,844,617 A | 7/1989 | Keldermann et al. | |
| 5,239,178 A | 8/1993 | Derndinger et al. | |
| 5,312,249 A | 5/1994 | Kennedy | |
| 5,338,198 A | 8/1994 | Wu et al. | |
| 5,353,073 A | 10/1994 | Kobayashi et al. | |
| 5,372,502 A * | 12/1994 | Massen et al. | 433/215 |
| 5,381,236 A | 1/1995 | Morgan | |
| 5,386,292 A | 1/1995 | Massen et al. | |
| 5,388,988 A | 2/1995 | Goisser et al. | |
| 5,573,493 A | 11/1996 | Sauer et al. | |
| 5,613,936 A * | 3/1997 | Czarnek et al. | 600/166 |
| 5,671,056 A * | 9/1997 | Sato | 356/602 |
| 5,737,084 A * | 4/1998 | Ishihara | 356/609 |
| 5,738,678 A | 4/1998 | Patel | |
| 5,801,880 A | 9/1998 | Matsuda et al. | |
| 6,263,234 B1 | 7/2001 | Engelhardt et al. | |
| 6,697,164 B1 | 2/2004 | Babayoff et al. | |
| 6,885,464 B1 * | 4/2005 | Pfeiffer et al. | 356/602 |
| 6,940,611 B2 | 9/2005 | Babayoff et al. | |
| 6,977,732 B2 | 12/2005 | Chen et al. | |
| 7,092,107 B2 * | 8/2006 | Babayoff et al. | 356/609 |
| 7,184,150 B2 | 2/2007 | Quadling et al. | |
| 7,230,725 B2 | 6/2007 | Babayoff et al. | |
| 7,319,529 B2 * | 1/2008 | Babayoff | 356/601 |
| 7,477,402 B2 | 1/2009 | Babayoff et al. | |
| 7,511,829 B2 * | 3/2009 | Babayoff | 356/601 |
| 7,630,089 B2 | 12/2009 | Babayoff et al. | |
| 7,724,378 B2 * | 5/2010 | Babayoff | 356/601 |
| 7,796,277 B2 | 9/2010 | Babayoff et al. | |
| 7,944,569 B2 | 5/2011 | Babayoff et al. | |
| 7,990,548 B2 | 8/2011 | Babayoff et al. | |
| 8,310,683 B2 | 11/2012 | Babayoff et al. | |

FOREIGN PATENT DOCUMENTS

| | | |
|---|---|---|
| DE | 19627568 A1 | 1/1998 |
| DE | 19638758 A1 | 3/1998 |
| DE | 19640495 A1 | 4/1998 |
| DE | 19650391 A1 | 6/1998 |
| EP | 0278882 A1 | 8/1988 |
| EP | 0679864 A1 | 11/1995 |
| GB | 2144537 A | 3/1985 |
| GB | 2321517 A | 7/1998 |
| JP | 07-229720 A | 8/1995 |
| JP | 10-009827 A | 1/1998 |
| WO | WO 93/11403 A1 | 6/1993 |
| WO | WO 97/37264 A1 | 10/1997 |
| WO | WO 98/25171 A1 | 6/1998 |

OTHER PUBLICATIONS

Gu et al., "Optimization of axial resolution in confocal imaging using annular pupils," Optik, 1993, pp. 87-90, vol. 93.

Ishihara et al., "High-speed 3D shape measurement using a non-scanning multiple-beam confocal imaging system," SPIE, 1998, pp. 68-75, vol. 3478.

Jervnall, J. and L. Selanne "Laser confocal microscopy and geographic information systems in the study of dental morphology," Palaeontologica electronica, 1999, vol. 2(1) [online] Retrieved from the Internet<URL:http://www.biocenter.helsinki.fi/bi/evodevo/pdf/pe99.pdf>.

Keyence America, "LT-9000 Series Lasar Displacement Sensor," Produce Brochure. Dec. 26, 2006.

Keyence, "How does the LT differ from conventional sensors?" Dec. 26, 2006. pp. 2-3.

Norman, et al., "The Fundamental Inventive Principles of CERBC CAD/CI M and other CAD/CAM Methods," 1996, pp. 81, 82, 88, 93.

Okuda et al., "Evaluation of in vitro secondary caries using confocal laser scanning microscope and X-ray analytical microscope" Journal of Dentistry, 2003, pp. 191-196, vol. 16(3).

Preston et al., "CAD/CAM in Dentistry," Applied Optics, 1996, pp. 77-77, vol. 89.

Sheppard, et al., "Three-dimensional imaging in confocal microscopy," Con focal Microscopy, 1990, Chapter 4, pp. 143-169, Academic Press Limited, San Diego, California, USA.

Tiziani, et al., "Three-dimensional analysis by a microlens-array confocal arrangement," Applied Optics, 1994, pp. 567-572, vol. 33 (4).

Tiziani, et al., "Three-dimensional image sensing by chromatic confocal microscopy," Applied Optics, 1994, pp. 1838-1843, vol. 33 (10).

Watson, T.F. and A. Boyde, "Confocal light microscopic techniques for examining dental operative procedures and dental materials. A status report for the American Journal of Dentistry," American Journal of Dentistry, 1991, pp. 193-200, vol. 4(4).

Watson, T.F., "Applications of confocal scanning optical microscopy to dentistry," British Dental Journal, 1991, pp. 287-291, vol. 171 (9). (Abstract only).

Office action dated Feb. 25, 2008 for U.S. Appl. No. 11/652,055.
Office action dated Apr. 2, 2012 for U.S. Appl. No. 13/082,623.
Office action dated Jun. 19, 2006 for U.S. Appl. No. 11/377,403.
Office action dated Sep. 1, 2010 for U.S. Appl. No. 12/654,698.
Office action dated Sep. 2, 2010 for U.S. Appl. No. 12/654,699.
Office action dated Sep. 29, 2009 for U.S. Appl. No. 12/314,064.
Office action dated Oct. 7, 2011 for U.S. Appl. No. 13/082,623.
U.S. Appl. No. 13/784,511, filed Mar. 4, 2013, Babayoff et al.

* cited by examiner

METHOD AND APPARATUS FOR IMAGING THREE-DIMENSIONAL STRUCTURE

CROSS-REFERENCE

This application is a Continuation Application of U.S. patent application Ser. No. 13/082,623, filed on Apr. 8, 2011, which was a Continuation Application of U.S. patent application Ser. No. 12/654,699, filed on Dec. 29, 2009, now U.S. Pat. No. 7,944,569 which was a Continuation Application of U.S. patent application Ser. No. 12/314,064, filed on Dec. 3, 2008, now U.S. Pat. No. 7,796,277, which was a Continuation Application of U.S. patent application Ser. No. 11/652,055, filed on Jan. 11, 2007, now U.S. Pat. No. 7,477,402, which was a Continuation Application of U.S. patent application Ser. No. 11/377,403, filed on Mar. 17, 2006, now U.S. Pat. No. 7,230,725, which was a Continuation Application of U.S. patent application Ser. No. 11/175,186, filed on Jul. 7, 2005, now U.S. Pat. No. 7,092,107, which was a Continuation Application of U.S. patent application Ser. No. 10/692,678, filed on Oct. 27, 2003, now U.S. Pat. No. 6,940,611, which was a Divisional Application of U.S. patent application Ser. No. 09/775,298, filed on Feb. 1, 2001, now U.S. Pat. No. 6,697,164, which was a Continuation Application of International PCT Application No. PCT/IL99/00431, filed on Aug. 5, 1999, which claims priority from Israeli Patent Application No. 125659, filed on Aug. 5, 1998, the content of each of which is hereby incorporated by reference in its entirety.

FIELD OF THE INVENTION

This invention in the field of imaging techniques and relates to a method and an apparatus for non-contact imaging of three-dimensional structures, particularly useful for direct surveying of teeth.

BACKGROUND OF THE INVENTION

A great variety of methods and systems have been developed for direct optical measurement of teeth and the subsequent automatic manufacture of dentures. The term "direct optical measurement" signifies surveying of teeth in the oral cavity of a patient. This facilitates the obtainment of digital constructional data necessary for the computer-assisted design (CAD) or computer-assisted manufacture (CAM) of tooth replacements without having to make any cast impressions of the teeth. Such systems typically includes an optical probe coupled to an optical pick-up or receiver such as charge coupled device (CCD) and a processor implementing a suitable image processing technique to design and fabricate virtually the desired product.

One conventional technique of the kind specified is based on a laser-triangulation method for measurement of the distance between the surface of the tooth and the optical distance probe, which is inserted into the oral cavity of the patient. The main drawback of this technique consists of the following. It is assumed that the surface of the tooth reflects optimally, e.g. Lambert's reflection. Unfortunately, this is not the case in practice and often the data that is obtained is not accurate.

Other techniques, which are embodied in CEREC-1 and CEREC-2 systems commercially available from Siemens GmbH or Sirona Dental Systems, utilize the light-section method and phase-shift method, respectively. Both systems employ a specially designed hand-held probe to measure the three-dimensional coordinates of a prepared tooth. However, the methods require a specific coating (i.e. measurement powder and white-pigments suspension, respectively) to be deposited to the tooth. The thickness of the coating layer should meet specific, difficult to control requirements, which leads to inaccuracies in the measurement data.

By yet another technique, mapping of teeth surface is based on physical scanning of the surface by a probe and by determining the probe's position, e.g. by optical or other remote sensing means, the surface may be imaged.

U.S. Pat. No. 5,372,502 discloses an optical probe for three-dimensional surveying. The operation of the probe is based on the following. Various patterns are projected onto the tooth or teeth to be measured and corresponding plurality of distorted patterns are captured by the probe. Each interaction provides refinement of the topography.

SUMMARY OF THE INVENTION

The present invention is directed to a method and apparatus for imaging three-dimensional structures. A preferred, non-limiting embodiment, is concerned with the imaging of a three-dimensional topology of a teeth segment, particularly such where one or more teeth are missing. This may allow the generation of data for subsequent use in design and manufacture of, for example, prosthesis of one or more teeth for incorporation into said teeth segment. Particular examples are the manufacture of crowns or bridges.

The present invention provides, by a first of its aspects, a method for determining surface topology of a portion of a three-dimensional structure, comprising:

(a) providing an array of incident light beams propagating in an optical path leading through a focusing optics and a probing face; the focusing optics defining one or more focal planes forward said probing face in a position changeable by said optics, each light beam having its focus on one of said one or more focal plane; the beams generating a plurality of illuminated spots on the structure;

(b) detecting intensity of returned light beams propagating from each of these spots along an optical path opposite to that of the incident light;

(c) repeating steps (a) and (b) a plurality of times, each time changing position of the focal plane relative to the structure; and (d) for each of the illuminated spots, determining a spot-specific position, being the position of the respective focal plane, yielding a maximum measured intensity of a respective returned light beam; and (e) based on the determined spot-specific positions, generating data representative of the topology of said portion.

By a further of its aspects, the present invention provides an apparatus for determining surface topology of a portion of a three-dimensional structure, comprising:

a probing member with a sensing face;

an illumination unit for providing an array of incident light beams transmitted towards the structure along an optical path through said probing unit to generate illuminated spots on said portion;

a light focusing optics defining one or more focal planes forward said probing face at a position changeable by said optics, each light beam having its focus on one of said one or more focal plane;

a translation mechanism coupled to said focusing optics for displacing said focal plane relative to the structure along an axis defined by the propagation of the incident light beams;

a detector having an array of sensing elements for measuring intensity of each of a plurality of light beams returning from said spots propagating through an optical path opposite to that of the incident light beams;

a processor coupled to said detector for determining for each light beam a spot-specific position, being the position of the respective focal plane of said one or more focal planes yielding maximum measured intensity of the returned light beam, and based on the determined spot-specific positions, generating data representative of the topology of said portion.

The probing member, the illumination unit and the focusing optics and the translation mechanism are preferably included together in one device, typically a hand-held device. The device preferably includes also the detector.

The determination of the spot-specific positions in fact amounts to determination of the in-focus distance. The determination of the spot-specific position may be by measuring the intensity per se, or typically is performed by measuring the displacement (S) derivative of the intensity (I) curve (dI/dS) and determining the relative position in which this derivative function indicates a maximum maximum intensity. The term "spot-specific position (SSP)" will be used to denote the relative in-focus position regardless of the manner in which it is determined. It should be understood that the SSP is always a relative position as the absolute position depends on the position of the sensing face. However the generation of the surface topology does not require knowledge of the absolute position, as all dimensions in the cubic field of view are absolute.

The SSP for each illuminated spot will be different for different spots. The position of each spot in an X-Y frame of reference is known and by knowing the relative positions of the focal plane needed in order to obtain maximum intensity (namely by determining the SSP), the Z or depth coordinate can be associated with each spot and thus by knowing the X-Y-Z coordinates of each spot the surface topology can be generated.

In accordance with one embodiment, in order to determine the Z coordinate (namely the SSP) of each illuminated spot the position of the focal plane is scanned over the entire range of depth or Z component possible for the measured surface portion. In accordance with another embodiment the beams have components which each has a different focal plane. Thus, in accordance with this latter embodiment by independent determination of SSP for the different light components, e.g. 2 or 3 with respective corresponding 2 or 3 focal planes, the position of the focal planes may be changed by the focusing optics to scan only part of the possible depth range, with all focal planes together covering the expected depth range. In accordance with yet another embodiment, the determination of the SSP involves a focal plane scan of only part of the potential depth range and for illuminated spots where a maximum illuminated intensity was not reached, the SSP is determined by extrapolation from the measured values or other mathematical signal processing methods.

The method and apparatus of the invention are suitable for determining a surface topology of a wide variety of three-dimensional structures. A preferred implementation of method and apparatus of the invention are in determining surface topology of a teeth section.

In accordance with one embodiment of the invention, the method and apparatus are used to construct an object to be fitted within said structure. In accordance with the above preferred embodiment, such an object is at least one tooth or a portion of a tooth missing in the teeth section. Specific examples include a crown to be fitted on a tooth stump or a bridge to be fitted within teeth.

By one embodiment of the invention, the plurality of incident light beams are produced by splitting a parent beam. Alternatively, each incident light beam or a group of incident light beams may be emitted by a different light emitter. In accordance with a preferred embodiment, light emitted from a light emitter passes through a diffraction or refraction optics to obtain the array of light beams.

In accordance with one embodiment, the parent light beam is light emitted from a single light emitter. In accordance with another embodiment, the parent light beam is composed of different light components, generated by different light emitters, the different light components differing from one another by at least one detectable parameter. Such a detectable parameter may, for example be wavelength, phase, different duration or pulse pattern, etc. Typically, each of said light components has its focus in a plane differently distanced from the structure than other light components. In such a case, when the focal plane of the optics is changed, simultaneously the different ranges of depth (or Z component) will be scanned. Thus, in such a case, for each illuminated spot there will be at least one light component which will yield a maximum intensity, and the focal distance associated with this light component will then define the Z component of the specific spot.

In accordance with an embodiment of the invention the incident light beams are polarized. In accordance with this embodiment, typically the apparatus comprises a polarization filter for filtering out, from the returned light beams, light components having the polarization of the incident light, whereby light which is detected is that which has an opposite polarization to that of the incident light.

The data representative of said topology may be used for virtual reconstruction of said surface topology, namely for reconstruction within the computer environment. The reconstructed topology may be represented on a screen, may be printed, etc., as generally known per se. Furthermore, the data representative of said topology may also be used for visual or physical construction of an object to be fitted within said structure. In the case of the preferred embodiment noted above, where said structure is a teeth section with at least one missing tooth or tooth portion, said object is a prosthesis of one or more tooth, e.g. a crown or a bridge.

By determining surface topologies of adjacent portions, at times from two or more different angular locations relative to the structure, and then combining such surface topologies, e.g in a manner known per se, a complete three-dimensional representation of the entire structure may be obtained. Data representative of such a representation may, for example, be used for virtual or physical reconstruction of the structure; may be transmitted to another apparatus or system for such reconstruction, e.g. to a CAD/CAM apparatus. Typically, but not exclusively, the apparatus of the invention comprises a communication port for connection to a communication network which may be a computer network, a telephone network, a wireless communication network, etc.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1A:
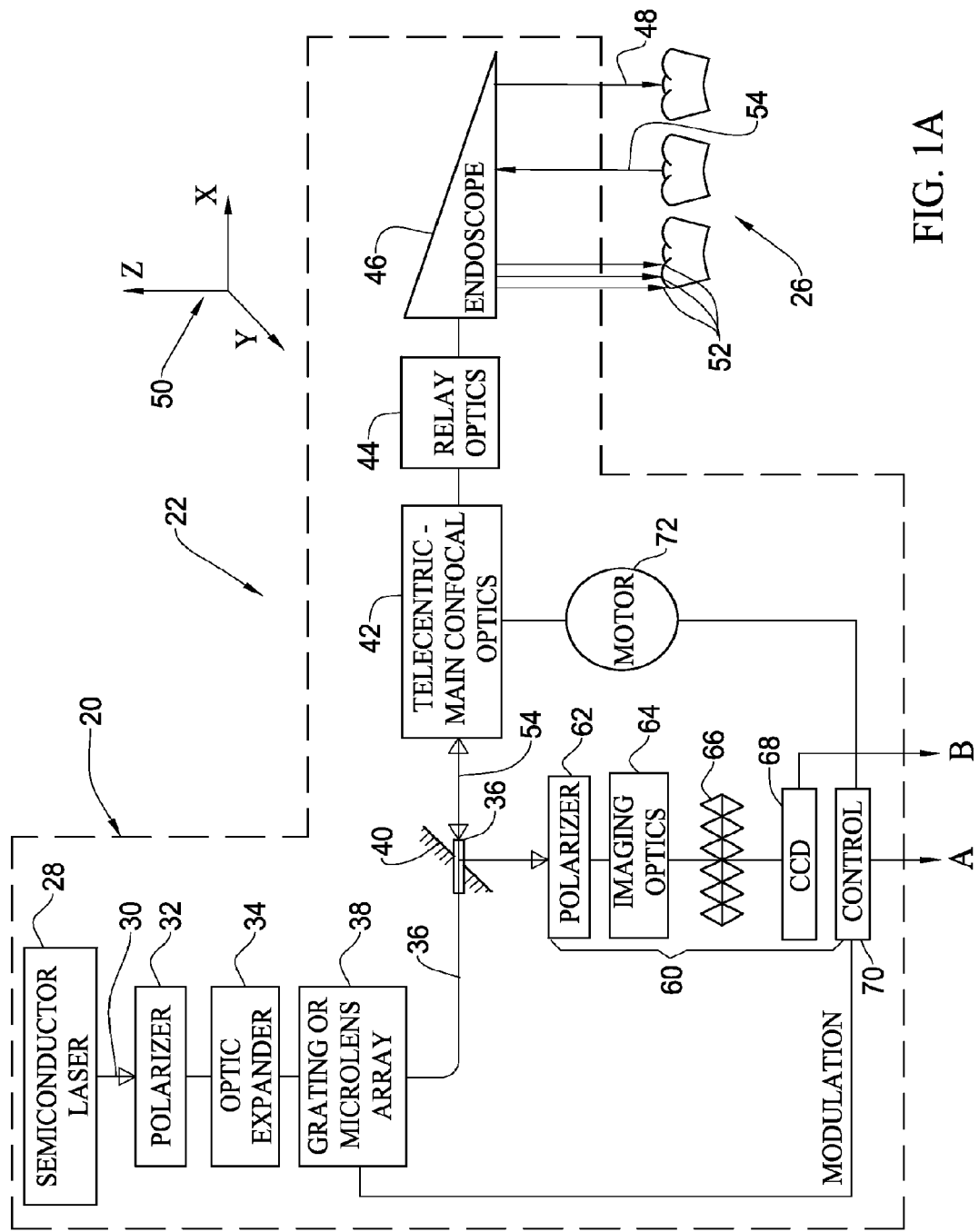
FIGS. 1A and 1B are a schematic illustration by way of a block diagram of an apparatus in accordance with an embodiment of the invention (FIG. 1B is a continuation of FIG. 1A)
Figure 1B:
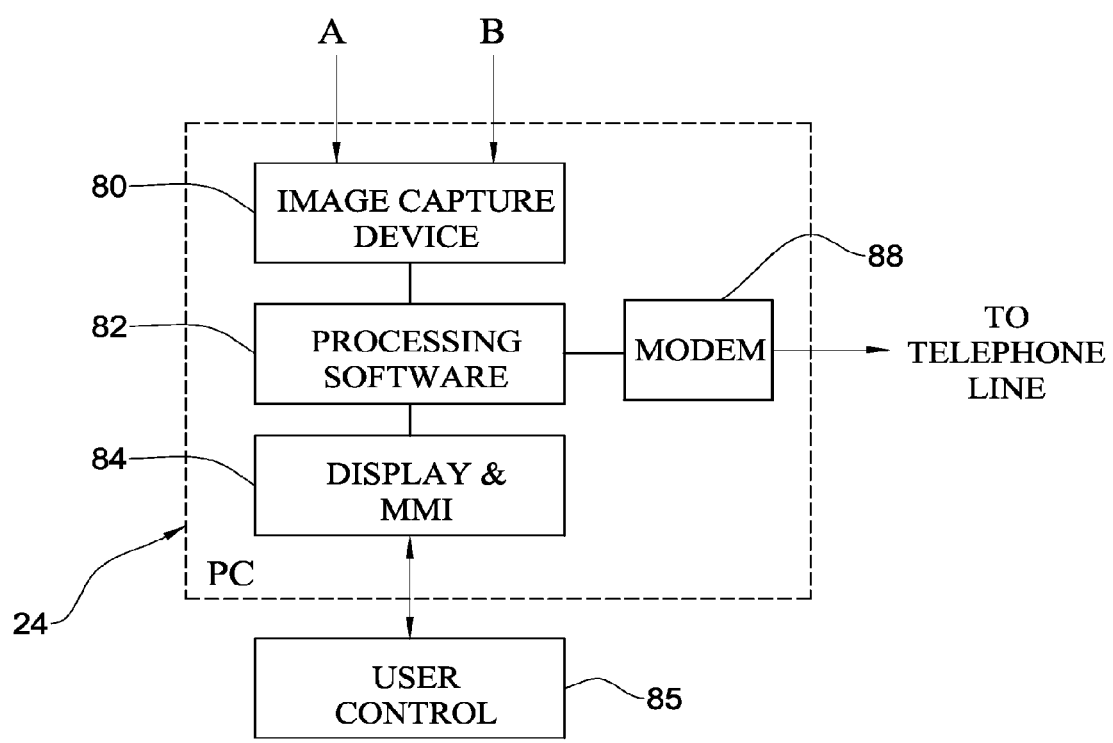

Reference is first being made to FIGS. 1A and 1B illustrating, by way of a block diagram an apparatus generally designated 20, consisting of an optical device 22 coupled to a processor 24. The embodiment illustrated in FIG. 1 is particularly useful for determining the three-dimensional structure of a teeth segment 26, particularly a teeth segment where at least one tooth or portion of tooth is missing for the purpose of generating data of such a segment for subsequent use in design or manufacture of a prosthesis of the missing at least one tooth or portion, e.g. a crown or a bridge. It should however be noted, that the invention is not limited to this embodiment, and applies, mutatis mutandis, also to a variety of other applications of imaging of three-dimensional structure of objects, e.g. for the recordal or archeological objects, for imaging of a three-dimensional structure of any of a variety of biological tissues, etc.

Optical device 22 comprises, in this specific embodiment, a semiconductor laser unit 28 emitting a laser light, as represented by arrow 30. The light passes through a polarizer 32 which gives rise to a certain polarization of the light passing through polarizer 32. The light then enters into an optic expander 34 which improves the numerical aperture of the light beam 30. The light beam 30 then passes through a module 38, which may, for example, be a grating or a micro lens array which splits the parent beam 30 into a plurality of incident light beams 36, represented here, for ease of illustration, by a single line. The operation principles of module 38 are known per se and the art and these principles will thus not be elaborated herein.

The light unit 22 further comprises a partially transparent mirror 40 having a small central aperture. It allows transfer of light from the laser source through the downstream optics, but reflects light travelling in the opposite direction. It should be noted that in principle, rather than a partially transparent mirror other optical components with a similar function may also be used, e.g. a beam splitter. The aperture in the mirror 40 improves the measurement accuracy of the apparatus. As a result of this mirror structure the light beams will yield a light annulus on the illuminated area of the imaged object as long as the area is not in focus; and the annulus will turn into a completely illuminated spot once in focus. This will ensure that a difference between the measured intensity when out-of- and in-focus will be larger. Another advantage of a mirror of this kind, as opposed to a beam splitter, is that in the case of the mirror internal reflections which occur in a beam splitter are avoided, and hence the signal-to-noise ratio improves.

The unit further comprises a confocal optics 42, typically operating in a telecentric mode, a relay optics 44, and an endoscopic probing member 46. Elements 42, 44 and 46 are generally as known per se. It should however be noted that telecentric confocal optics avoids distance-introduced magnification changes and maintains the same magnification of the image over a wide range of distances in the Z direction (the Z direction being the direction of beam propagation). The relay optics enables to maintain a certain numerical aperture of the beam's propagation.

The endoscopic probing member typically comprises a rigid, light-transmitting medium, which may be a hollow object defining within it a light transmission path or an object made of a light transmitting material, e.g. a glass body or tube. At its end, the endoscopic probe typically comprises a mirror of the kind ensuring a total internal reflection and, which thus directs the incident light beams towards the teeth segment 26. The endoscope 46 thus emits a plurality of incident light beams 48 impinging on to the surface of the teeth section.

Incident light beams 48 form an array of light beams arranged in an X-Y plane, in the Cartasian frame 50, propagating along the Z axis. As the surface on which the incident light beams hits is an uneven surface, the illuminated spots 52 are displaced from one another along the Z axis, at different $(X_i, Y_i)$ locations. Thus, while a spot at one location may be in focus of the optical element 42, spots at other locations may be out-of-focus. Therefore, the light intensity of the returned light beams (see below) of the focused spots will be at its peak, while the light intensity at other spots will be off peak. Thus, for each illuminated spot, a plurality of measurements of light intensity are made at different positions along the Z-axis and for each of such $(X_i, Y_i)$ location, typically the derivative of the intensity over distance (Z) will be made, the $Z_i$ yielding maximum derivative, $Z_0$, will be the in-focus distance. As pointed out above, where, as a result of use of the punctured mirror 40, the incident light forms a light disk on the surface when out of focus and a complete light spot only when in focus, the distance derivative will be larger when approaching in-focus position thus increasing accuracy of the measurement.

The light scattered from each of the light spots includes a beam travelling initially in the Z axis along the opposite direction of the optical path traveled by the incident light beams. Each returned light beam 54 corresponds to one of the incident light beams 36. Given the unsymmetrical properties of mirror 40, the returned light beams are reflected in the direction of the detection optics generally designated 60. The detection optics comprises a polarizer 62 that has a plane of preferred polarization oriented normal to the plane polarization of polarizer 32. The returned polarized light beam 54 pass through an imaging optic 64, typically a lens or a plurality of lenses, and then through a matrix 66 comprising an array of pinholes. CCD camera has a matrix or sensing elements each representing a pixel of the image and each one corresponding to one pinhole in the array 66.

The CCD camera is connected to the image-capturing module 80 of processor unit 24. Thus, each light intensity measured in each of the sensing elements of the CCD camera, is then grabbed and analyzed, in a manner to be described below, by processor 24.

Unit 22 further comprises a control module 70 connected to a controlling operation of both semi-conducting laser 28 and a motor 72. Motor 72 is linked to telecentric confocal optics 42 for changing the relative location of the focal plane of the optics 42 along the Z-axis. In a single sequence of operation, control unit 70 induces motor 72 to displace the optical element 42 to change the focal plane location and then, after receipt of a feedback that the location has changed, control module 70 will induce laser 28 to generate a light pulse. At the same time it will synchronize image-capturing module 80 to grab data representative of the light intensity from each of the sensing elements. Then in subsequent sequences the focal plane will change in the same manner and the data capturing will continue over a wide focal range of optics 44, 44.

Image capturing module 80 is connected to a CPU 82 which then determines the relative intensity in each pixel over the entire range of focal planes of optics 42, 44. As explained above, once a certain light spot is in focus, the measured intensity will be maximal. Thus, by determining the $Z_i$, corresponding to the maximal light intensity or by determining the maximum displacement derivative of the light intensity, for each pixel, the relative position of each light spot along the Z axis can be determined. Thus, data representative of the three-dimensional pattern of a surface in the teeth segment, can be obtained. This three-dimensional representation may be displayed on a display 84 and manipulated for viewing, e.g. viewing from different angles, zooming-in or out, by the user control module 86 (typically a computer keyboard). In addition, the data representative of the surface topology may be transmitted through an appropriate data port, e.g. a modem 88, through any communication network, e.g. telephone line 90, to a recipient (not shown) e.g. to an off-site CAD/CAM apparatus (not shown).

By capturing, in this manner, an image from two or more angular locations around the structure, e.g. in the case of a teeth segment from the buccal direction, from the lingal direction and optionally from above the teeth, an accurate three-dimensional representation of the teeth segment may be reconstructed. This may allow a virtual reconstruction of the three-dimensional structure in a computerized environment or a physical reconstruction in a CAD/CAM apparatus.

As already pointed out above, a particular and preferred application is imaging of a segment of teeth having at least one missing tooth or a portion of a tooth, and the image can then be used for the design and subsequent manufacture of a crown or any other prosthesis to be fitted into this segment.

Figure 2A:
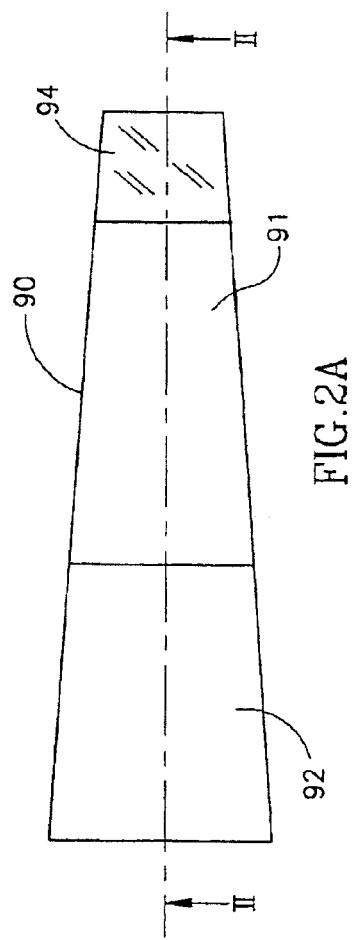
FIG. 2A is a top view of a probing member in accordance with an embodiment of the invention.
Figure 2B:
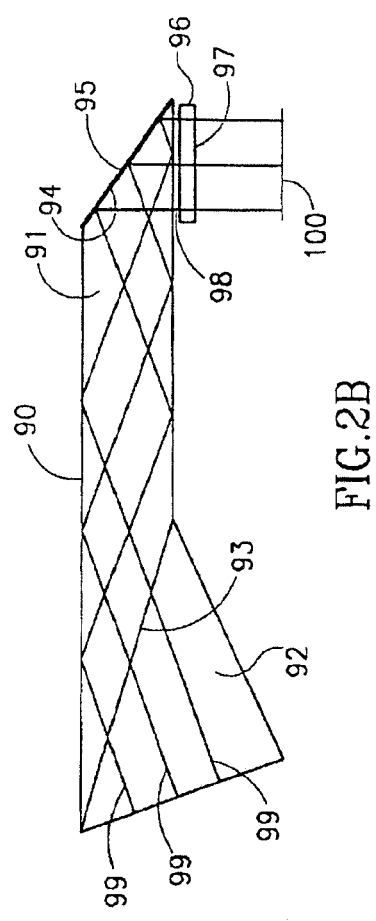
FIG. 2B is a longitudinal cross-section through line II-II in FIG. 2A, depicting also some exemplary rays passing therethrough.

Reference is now being made to FIGS. 2A AND 2B illustrating a probing member 90 in accordance with one, currently preferred, embodiment of the invention. The probing member 90 is made of a light transmissive material, typically glass and is composed of an anterior segment 91 and a posterior segment 92, tightly glued together in an optically transmissive manner at 93. Slanted face 94 is covered by a totally reflective mirror layer 95. Glass disk 96 defining a sensing surface 97 is disposed at the bottom in a manner leaving an air gap 98. The disk is fixed in position by a holding structure which is not shown. Three light rays are 99 are represented schematically. As can be seen, they bounce at the walls of the probing member at an angle in which the walls are totally reflective and finally bounce on mirror 94 and reflected from there out through the sensing face 97. The light rays focus on focusing plane 100, the position of which can be changed by the focusing optics (not shown in this figure).

Figure 3:
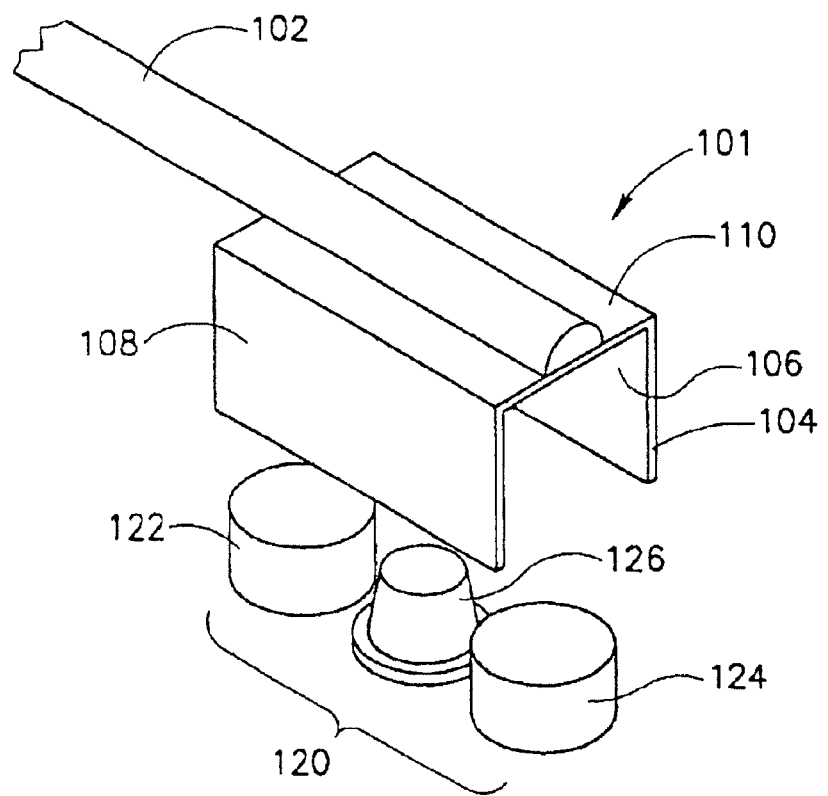
FIG. 3 is a schematic illustration of another embodiment of a probing member.

Reference is now being made to FIG. 3, which is a schematic illustration of an endoscopic probe in accordance with an embodiment of the invention. The endoscopic probe, generally designated 101, has a stem 102 defining a light transmission path (e.g., containing a void elongated space, being made of or having an interior made of a light transmitting material. Probe 102 has a trough-like probe end 104 with two lateral probe members 106 and 108 and a top probe member 110. The optical fibers have light emitting ends in members 106, 108 and 110 whereby the light is emitted in a direction normal to the planes defined by these members towards the interior of the trough-like structure 104. The probe is placed over a teeth segment 120, which in the illustrated case consists of two teeth 122 and 124, and a stamp 126 of a tooth for placement of a crown thereon. Such a probe will allow the simultaneous imaging of the surface topology of the teeth segment from three angles and subsequently the generation of a three-dimensional structure of this segment.

Figure 4:
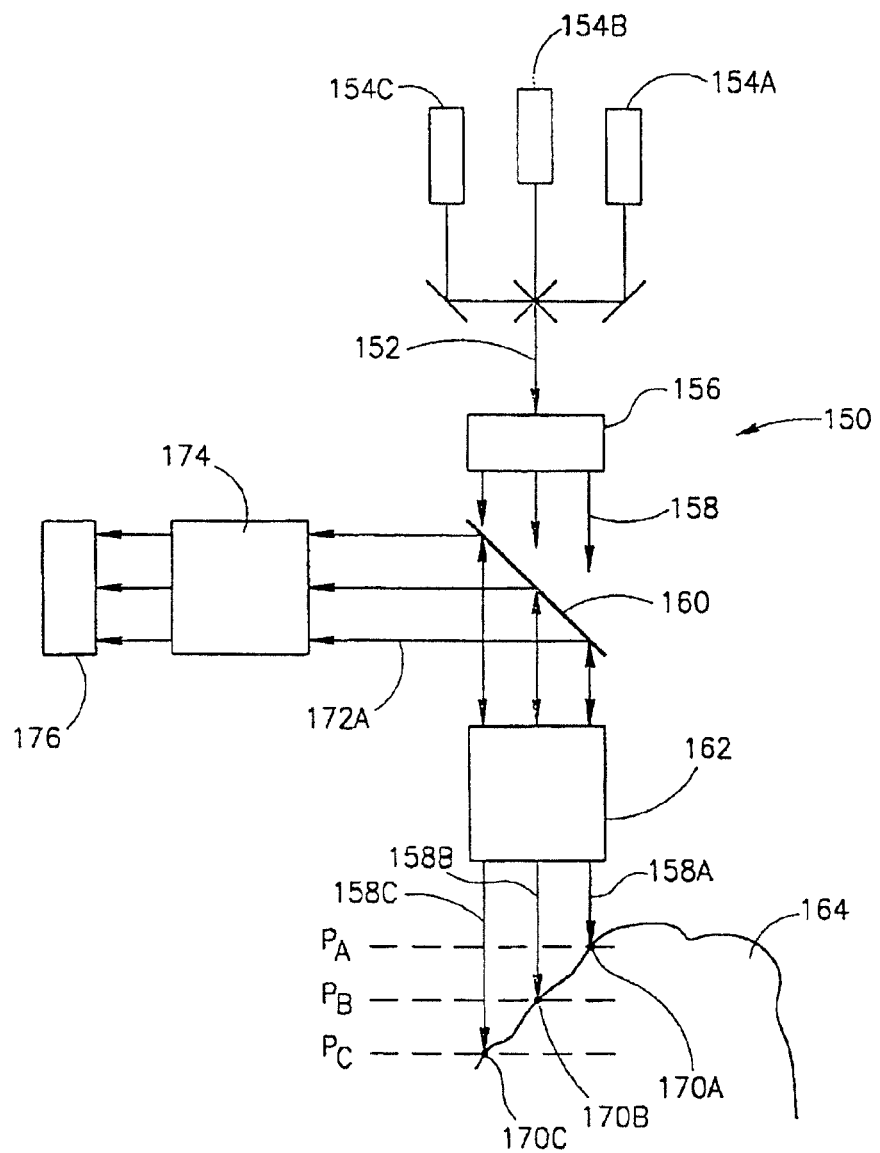
FIG. 4 is a schematic illustration of an embodiment where the parent light beam, and thus each of the incident light beams, is composed of several light components, each originating from a different light emitter.

Reference is now being made to FIG. 4. In this figure, a number of components of an apparatus generally designated 150 in accordance with another embodiment are shown. Other components, not shown, may be similar to those of the embodiment shown in FIG. 1. In this apparatus a parent light beam 152 is a combination of light emitted by a number of laser light emitters 154A, 154B and 154C. Optic expander unit 156 then expands the single parent beam into an array of incident light beams 158. Incident light beams pass through unidirectional mirror 160, then through optic unit 162 towards object 164.

The different light components composing parent beam 152 may for example be different wavelengths, a different one transmitted from each of laser emitters 154A-C. Thus, parent light beam 152 and each of incident light beams 158 will be composed of three different light components. The image of the optics, or an optical arrangement associated with each of light emitters may be arranged such that each light component focuses on a different plane, $P_A$, $P_B$ and $P_C$, respectively. Thus in the position shown in FIG. 3, incident light beam 158A bounces on the surface at spot 170A which in the specific optical arrangement of optics 162 is in the focal point for light component A (emitted by light emitter 154A). Thus, the returned light beam 172A, passing through detection optics 174 yield maximum measured intensity of light component A measured by two-dimensional array of spectrophotometers 176, e.g. a 3 CHIP CCD camera. Similarly, different maximal intensity will be reached for spots 170B and 170C for light components B and C, respectively.

Thus, by using different light components each one focused simultaneously at a different plane, the time measurement can be reduced as different focal plane ranges can simultaneously be measured.

What is claimed is:

1. An apparatus for imaging at least a portion of a patient's dentition, the apparatus comprising:
   an illumination unit configured to transmit a parent light beam comprising a first wavelength component and a second wavelength component;
   an optical system configured to generate an illuminated region on a portion of a patient's dentition, wherein the first wavelength component is focused at a first focal plane and the second wavelength component is focused at a second focal plane;
   a translation mechanism configured to move the position of the first focal plane and the second focal plane at the same time over a range of focal plane positions;
   a detector unit configured to measure intensity of returned light beams of the first wavelength component and the second wavelength component; and
   a processor coupled to the detector unit and configured to determine a surface topology of the patient's dentition based at least in part on a first intensity of a first returned light beam of the first wavelength component and a second intensity of a second returned light beam of the second wavelength component.

2. The apparatus of claim 1, wherein the apparatus comprises a hand held probe including one or more of the illumination unit, the optical system, the translation mechanism, the detector unit and the processor.

3. The apparatus of claim 1, further comprising a probing member having a sensing face, wherein the illuminated region on the portion of the patient's dentition is forward of the sensing face.

4. The apparatus of claim 1, further comprising an optics expander unit configured to expand the parent light beam into an array of incident light beams, each comprising the first wavelength component and the second wavelength component.

5. The apparatus of claim 4, wherein the optics expander unit comprises a grating or a microlens array.

6. The apparatus of claim 1, wherein the translation mechanism comprises a motor.

7. The apparatus of claim 1, wherein the illuminated region is oriented in an X-Y plane and the first focal plane and the second focal plane are located at a first position and a second position, respectively, along a depth dimension substantially orthogonal to the X-Y plane.

8. The apparatus of claim 7, wherein the location of the first position and the second position along the depth dimension is defined by the first wavelength component and the second wavelength component, respectively.

9. The apparatus of claim 7, wherein the processor is further configured to determine a surface topology of the patient's dentition based on a distance between the first focal plane and the second focal plane along the depth dimension.

10. The apparatus of claim 7, wherein the processor is configured to determine the surface topology of the patient's dentition based on an intensity profile of the first returned light beam and the second returned light beam, each intensity profile being generated by moving the first focal plane and the second focal plane along the depth dimension relative to the patient's dentition.

11. The apparatus of claim 1, wherein the processor is configured to determine the surface topology of the patient's dentition based at least in part on a first maximum intensity of the first returned light beam and a second maximum intensity of the second returned light beam.

12. The apparatus of claim 1, wherein the processor is configured to determine the surface topology of the patient's dentition based at least in part on a derivative of the first intensity of the first returned light beam and a derivative of the second intensity of the second returned light beam.

13. The apparatus of claim 1, wherein the parent light beam further comprises a third wavelength component and the optical system is further configured to focus the third wavelength component at a third focal plane.

14. The apparatus of claim 1, wherein the illumination unit comprises a first light emitter to generate the first wavelength component and a second light emitter to generate the second wavelength component.

15. The apparatus of claim 14, wherein the first light emitter comprises a first laser and the second light emitter comprises a second laser.

16. The apparatus of claim 1, wherein the detector unit comprises a CCD camera.

17. An apparatus for determining surface topology of at least a portion of a three-dimensional structure, the apparatus comprising:
a probing member having a sensing face;
an illumination unit configured to transmit a parent light beam along an optical path in the hand-held probe;
a module positioned in the optical path and configured to generate a plurality of incident light beams;
an optical system configured to focus the plurality of incident light beams at a focal plane forward of the sensing face;
a detector unit configured to measure intensities of a plurality of returned light beams that are generated from illuminating the portion of the three-dimensional structure with the plurality of incident light beams; and
a processor coupled to the detector unit and configured to determine a surface topology of the three-dimensional structure based at least in part on the measured intensities of the plurality of returned light beams.

18. The apparatus of claim 17, wherein the detector unit comprises a plurality of sensor elements, each sensor element being configured to measure intensity from a corresponding returned light beam in the plurality of returned light beams.

19. The apparatus of claim 17, wherein the optical system comprises a translation mechanism configured to change the focal plane of the plurality of incident light beams over a range of focal plane positions.

20. The apparatus of claim 19, wherein the translation mechanism is further configured to change the focal plane of the plurality of incident light beams while maintaining a fixed distance between the hand-held probe and the three-dimensional structure.

21. The apparatus of claim 19, wherein the translation mechanism comprises a motor.

22. The apparatus of claim 17, wherein the optical system is configured to operate in telecentric mode.

23. The apparatus of claim 17, wherein the module is configured to produce a pattern of the plurality of incident light beams.

24. The apparatus of claim 19, wherein the intensities of the plurality of returned light beams depends on the position of the focal plane of the plurality of incident light beams, and the processor is further configured to determine the surface topology based on the maximum intensity of each returned light beam measured over the range of focal plane positions.

25. The apparatus of claim 17, further comprising a polarization optic configured to polarize the plurality of incident light beams.

* * * * *